United States Patent [19]

Kleinschroth et al.

[11] Patent Number: 4,677,108

[45] Date of Patent: Jun. 30, 1987

[54] 4-OXO-PYRIDO[2,3-d]PYRIMIDINONE DERIVATIVES

[75] Inventors: Jürgen Kleinschroth; Gerhard Satzinger, both of Denzlingen; Karl Mannhardt, Elzach-Oberprechtal; Johannes Hartenstein, Stegen-Wittental; Hartmut Osswald, Waldkirch; Günter Weinheimer, Denzlingen; Edgar Fritschi, St. Peter, all of Fed. Rep. of Germany

[73] Assignee: Warner-Lambert Company, Morris Plains, N.J.

[21] Appl. No.: 787,845

[22] Filed: Oct. 16, 1985

[30] Foreign Application Priority Data

Oct. 19, 1984 [DE] Fed. Rep. of Germany ....... 3438350

[51] Int. Cl.$^4$ .................. A61K 31/435; C07D 471/04
[52] U.S. Cl. ..................................... 514/258; 544/279
[58] Field of Search ......................... 514/258; 544/279

[56] References Cited

U.S. PATENT DOCUMENTS 4,361,700 11/1982 Purcell et al. ........................ 544/279
4,560,753 12/1985 Lesher et al. ....................... 544/279

OTHER PUBLICATIONS

Gorlitzer et al., *Arch. Pharm.* (Weinheim), vol. 314, pp. 938–949, (1981).

*Primary Examiner*—Donald G. Daus
*Assistant Examiner*—Barbara Cassatt
*Attorney, Agent, or Firm*—Elizabeth M. Anderson

[57] ABSTRACT

4-Oxo-pyrido[2,3-d]pyrimidine derivatives are herein described as well as processes for their preparation.

These compounds possess valuable pharmacological properties. As calcium antagonists they exert vasospasmolytic, vasodilatory, and antihypertensive activities. Surprisingly some of the compounds also have the effect of increasing contractility. They are therefore particularly suited for the treatment of vascular diseases.

5 Claims, No Drawings

4-OXO-PYRIDO[2,3-D]PYRIMIDINONE DERIVATIVES

SUMMARY OF THE INVENTION

The invention concerns new 4-oxo-pyrido-[2,3-d]pyrimidine derivatives of the general Formula I

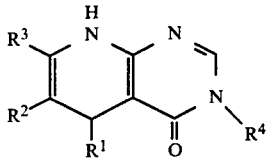

wherein
$R^1$ represents an unsubstituted or substituted aromatic or heteroaromatic ring;
$R^2$ a nitrile group, a carboxyl group or an alkoxycarbonyl residue with up to six carbon atoms;
$R^3$ a straight-chained or branched alkyl group with up to four carbon atoms or an amino group; and
$R^4$ is hydrogen, an alkyl, alkoxyalkyl or a substituted or unsubstituted aminoalkyl group;
as well as optionally the pharmacologically acceptable safe salts thereof.

Another subject matter of the present invention is a method of use of the above compounds of Formula I for the treatment of vascular diseases and pharmaceutical compositions containing the new compounds.

DETAILED DESCRIPTION

The compounds of the present invention may be prepared from a process for the preparation of 4-oxo-pyrido[2,3-d]pyrimidine derivatives of the general Formula VI.

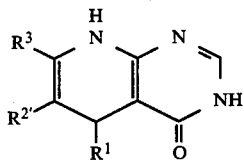

in which $R^1$ and $R^3$ have the above meaning and $R^{2'}$ represents a nitrile group or an alkoxycarbonyl residue with up to six carbon atoms, as well as a process for the preparation of compounds of the general Formula I, characterized by that compounds of the general Formula VI in a generally known manner are alkylated, aminoalkyalated, or alkoxyalkylated.

The compounds of the general Formula VI are prepared by either
(a) reacting a dihydropyridine of the general Formula V

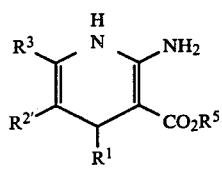

in which $R^1$, $R^{2'}$, $R^3$ and $R^5$ have the above meaning, with s-triazine in the presence of a base, or (b) condensing a compound of the general Formula VIII

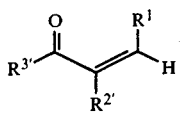

in which $R^1$ and $R^{2'}$ have the above meaning, and $R^{3'}$ represents a straight-chained or branched alkyl group with up to four carbon atoms, by heating in polar solvents with 6-amino-4-hydroxypyrimidine.

The compounds of the general Formula I are prepared in a generally known manner by alkylation, aminoalkylation, or alkoxyalkylation, of the compounds of the general Formula VI with compounds of the general Formula VII $$X-R^4 \qquad (VII)$$

in which $R^4$ has the above meaning and X represents halogen, in particular chlorine, bromine, or iodine, preferably in the presence of a hydrohalogenide acceptor.

Compounds of the general Formula I, in which $R^2$ represents a carboxyl group, are prepared by hydrolyzing compounds of the general Formula I, in which $R^2$ represents an alkoxycarbonyl residue suitable for the splitting of esters, in a generally known manner, preferably in an acid medium.

The compounds of the general Formula V (cf., e.g., "Liebig's Ann. Chem." 1977 p 1895; "Arzneim.-Forsch." 31 (II) 8 (1981) p 1173) and VIII (cf., e.g., "Arch. Pharm." 317 (1984), p 709) are known from literature or can be prepared in an analogous manner.

In order to perform reaction (a) the dihydropyridine derivative is heated to temperatures of between 50° and 160° C., preferably 100°–150° C., together with s-triazine in an inert organic solvent in the presence of strong bases such as, e.g., alkali alcoholates or sodium hydride in an inert organic solvent. Suitable solvents are mainly polar solvents such as dimethylsulfoxide, dimethylformamide, or ethyleneglycol dimethylether. This reaction produces, in addition to the compounds isolated as the main products, also compounds according to German Offenlegungsschrift No. 33 27 650, which are separated by chromatography.

The reaction (b) is performed by heating the two components in polar solvents, preferably in alcohols, at temperatures between 60° and 120° C.

The alkylation, aminoalkylation and alkoxyalkylation of the compounds of the general Formula VI is performed according to generally known methods, preferably using a hydrohalogenide acceptor. If suitable conditions are chosen for the reaction its couse is showing a high regional selectivity. The o-alkylation products to be expected are surprisingly formed only in low quantities. The products are separated and purified by means of chromatography and/or crystallization.

Acidic or basic compounds of the general Formula I, which for $R^2$ contain a carboxyl group, and for $R^4$ a substituted or unsubstituted aminoalkyl group, for the purpose of purification and for pharmacotechnological reasons are transferred preferably into crystalline, pharmaceutically acceptable salts.

In case $R^2$ represents a carboxyl group, bases such as, e.g., hydroxides or carbonates can be used to produce the corresponding salts of the alkali or alkaline-earth metals. If the residue $R^3$ or $R^4$ has the character of a base, salts are obtained in the usual manner by neutralization of the bases with corresponding inorganic or organic acids. As acids may be used, e.g., hydrochloric acid, sulphuric acid, phosphoric acid, hydrobromic acid, acetic acid, tartaric acid, lactic acid, citric acid, malic acid, salicylic acid, ascorbic acid, malonic acid, or succinic acid.

Since the comounds of the general Formula I according to the invention are showing a chiral center at C-5 they may be present either as racemic mixtures, or in the form of the enantiomers.

By unsubstituted or substituted aromatic or heteroaromatic ring, there is meant phenyl or phenyl substituted by up to three of the same or different groups selected from a straight or branched alkyl with up to four carbon atoms, halogen selected from fluorine, chlorine, bromine or iodine, nitro, a straight or branched alkoxy with up to four carbon atoms, difluoromethoxy, trifluoromethoxy, dialkylamino in which alkyl is as defined above, alkylthio in which alkyl is as defined above or trifluoromethyl, or a methylenedioxy group; or a pyridyl, e.g., 2-, 3-, or 4-pyridyl, or thienyl group (2- or 3-) which is unsubstituted or substituted by alkyl as defined above.

Alkyl wherever used and unless otherwise defined in the specification means a straight or branched hydrocarbon radical with up to six carbon atoms, such as, for example; methyl, ethyl, propyl, isopropyl, butyl, sec-butyl, isobutyl, tert-butyl, amyl, isoamyl, neopentyl, hexyl, and the like.

Preferred are compounds of the general Formula I, in which $R^1$ represents a phenyl residue, substituted preferably in two or three position by halogen, nitro, methyl, methoxy, difluoromethoxy, trifluoromethoxy, dimethylamino or diethylamino, methylthio, or trifluoromethyl, or disubstituted, preferably in 2,3 position by methoxy or methylenedioxy, or in 2,3 or 2,6 position by halogen atoms which may be the same or different;

$R^2$ represents a nitrile group, a carboxyl group or an alkoxy carbonyl residue, in particular a methoxy, ethoxy, isopropoxy, isobutoxy, or methoxyethoxy carbonyl residue;

$R^3$ represents a methyl or ethyl residue or an amino group;

$R^4$ represent hydrogen, a methyl, ethyl, n-propyl or isopropyl residue, a lower alkoxyalkyl group, in particular the ethoxyethyl group, or a substituted or unsubstituted aminoalkyl group, in particular the dimethylaminopropyl and the piperidinopropyl group.

The compounds of the General Formula I possess valuable pharmacological properties. Particularly when used as calcium antagonists they exert vasospasmolytic, vasodilatory, and antihypertensive activities. Surprisingly some of the compounds also have the effects of increasing the contractility.

For reason of their vasospasmolytic effects the compounds are mainly indicated for the treatment of cerebral, cardiac, and peripheral vascular diseases such as myocardial ischemia, cerebral infarction, pulmonary thromboses, as well as in cases of arteriosclerosis and other stenotic disorders.

The 4-oxo-pyrido[2,3-d]pyrimidine derivatives of the present invention are therefore valuable agents for combating cardiovascular mortality. Another subject-matter of the present invention is therefore the use of the 4-oxo-pyrido[2,3-d]pyrimidines of the general Formula I for the treatment of vascular diseases.

The compounds of the general Formula I according to the invention may be applied in liquid or solid form, orally or parenterally. For the solution for injection mainly water is used containing such additives as stabilizers, solubilizers, or buffers as are usual for injectable solutions.

Such additives are, e.g., tartrate and citrate buffers, ethanol, complex formers (such as ethylenediamine-tetraacetic acid and the nontoxic salts thereof) as well as high molecular weight polymers (such as liquid polyethylene oxide) to regulate the viscosity. Solid vehicles are, e.g., starch, lactose, mannitol, methyl cellulose, talcum, highly dispersed silicic acids, higher molecular weight fatty acids (such as stearic acid), gelatin, agar-agar, calcium phosphate, magnesium stearate, animal and vegetable fats, solid high molecular weight polymers (such as polyethylene glycol); if desired preparations suited for oral application may in addition contain flavors and/or sweetening agents.

Enterally administered single doses are in the order from about 5 to 250 mg, preferably 10–100 mg. Doses for parenteral application would be in the order from about 1 to 20 mg.

The following examples serve to illustrate the invention further.

EXAMPLE 1

($\pm$)-3,4,5,8-Tetrahydro-7-methyl-4-oxo-5-phenyl-pyrido[2,3-d]pyrimidine-6-carboxylic acid ethyl ester (process a)

To a stirred suspension of 4.5 g (150 mmol) sodium hydride (80% in liquid paraffin) in 75 ml dry dimethylformamide is added dropwise, and in nitrogen atmosphere, a solution of 40.6 g (123 mmol) ($\pm$)-2-amino-1,4-dihydro-6-methyl-4-phenyl-pyridine-3,5-dicarboxylic acid diethyl ester in 200 ml dimethylformamide. When the gas generation diminishes stirring is continued at room temperature for 30 minutes; subsequently 10.0 g (123 mmol) s-triazine in 250 ml dimethylformamide are added dropwise. The reaction mixture is heated to 110° C. for 16 hours and reduced under vacuum when cool. The dark residue is subjected to chromatography on silica gel with dichloromethane/methanol 95:5. The fraction of the $R_f$0.5 is isolated, heated to boiling with acetone, and the crystals precipitated after cooling are recrystallized from ethanol for the purpose of further purification.

This process yields ($\pm$)-3,4,5,8-tetrahydro-7-methyl-4-oxo-5-phenyl-pyrido[2,3-d]pyrimidine-6-carboxylic acid ethyl ester in the form of beige crystals with a mp of 303°–305° C. (decomposition).

Analogously the following compounds are obtained.
($\pm$)-5-(2-Fluorophenyl)-3,4,5,8-tetrahydro-7-methyl-4-oxo-pyrido[2,3-d]pyrimidine-6-carboxylic acid ethyl ester (1.a), process (a)
mp 264°–265° C. from ethanol.
($\pm$)-3,4,5,8-Tetrahydro-7-methyl-5-(2-nitrophenyl)-4-oxo-pyrido[2,3-d]pyrimidine-6-carboxylic acid ethyl ester (1.b), process (a)
mp 280°–282° C. from ethanol.
($\pm$)-3,4,5,8-Tetrahydro-7-methyl-4-oxo-5-(2-trifluoromethylphenyl)pyrido[2,3-d]pyrimidine-6-carboxylic acid methyl ester (1.c), process (a)
mp 294°–295° C. from acetic ethyl ester/ethanol.

(±)-7-Amino-3,4,5,8-tetrahydro-5-(2-methoxyphenyl)-4-oxo-pyrido[2,3-d]pyrimidine-6-carboxylic acid ethyl ester (1.d), process (a)
mp 283°-285° C. from ethanol.
(±)-3,4,5,8-Tetrahydro-7-methyl-5-(3-nitrophenyl)4-oxo-pyrido[2,3,-d]pyrimidine-6-carboxylic acid isopropyl ester (1.e), process (a)
mp 258°-260° C. from isopropanol.

EXAMPLE 2

(±)-3,4,5,8-Tetrahydro-7-methyl-5-(3-nitrophenyl)-4-oxo-pyrido[2,3-d]pyrimidine-6-carboxylic acid methyl ester (process b)

Seventeen and 0.5 g (70 mmol) 3-nitrobenzylidene aceto-acetic methyl ester and 7.8 g (70 mmol) 4-amino-6-hydroxypyrimidine are heated under reflux in 800 ml dry ethanol for 20 hours. The crystals precipitated after cooling yield, following recrystallization from ethanol, colorless needles of a mp of 289°-290° C.

EXAMPLE 3

(±)-5-(2-Fluorophenyl)-3,4,5,8-tetrahydro-3-isopropyl-7-methyl-4-oxo-pyrido[2,3-d]pyrimidine-6-carboxylic acid ethyl ester To a stirred suspension of 0.5 g (17 mmol) sodium hydride (80% in liquid paraffin) in 30 ml dry dimethylformamide is added dropwise a solution of 3.7 g (11 mmol) (±)-5-(2-fluorophenyl)-3,4,5,8-tetrahydro-7-methyl-4-oxo-pyrido[2,3-d]pyrimidine-6-carboxylic acid ethyl ester in 30 ml dimethylformamide. When the gas generation diminishes stirring at room temperature is continued for 30 minutes; subsequently 2.6 g (15 mmol) isopropyl iodide in 15 ml dimethylformamide are added dropwise. Stirring is continued at room temperature for 20 hours, the solvent is rotated off under vacuum, and the residue mixed with 100 ml water by stirring.

The crystals formed are filtered off, dried, dissolved in acetic acid ethyl ester and subjected to chromatography on silica gel with toluene/acetic acid ethyl ester 1:1.

The fraction of the $R_f0.3$ is isolated and recrystallized from diisopropyl ether/ethanol. This process yields (±)-5-(2-fluorophenyl)-3,4,5,8-tetrahydro-3-isopropyl-7-methyl-4-oxo-pyrido[2,3-d]pyrimidine-6-carboxylic acid ethyl ester in the form of colorless crystals with a mp of 178°-180° C.

Analogously the following compounds are obtained.
(±)-3,4,5,8-Tetrahydro-3-isopropyl-7-methyl-4-oxo-5-phenyl-pyrido[2,3-d]pyrimidine-6-carboxylic acid ethyl ester (3.a)
m.p. 184°-185° C. from diisopropyl ether/ethanol.
(±)-3,4,5,8-Tetrahydro-7-methyl-5-(3-nitrophenyl)-4-oxo-3-(3-piperidinopropyl - pyrido[2,3-d]pyrimidine-6-carboxylic acid isopropyl ester (3.b)
m.p. 143°-145° C. from diisopropyl ether.

The following comparison studies serve to illustrate the pharmacological efficacy of the compounds according to the general Formula I.

(a) Isolated Smooth Muscles (Table 1)

Of rabbits (vessel ring segments, a basilaris, a. coronaria, a. saphena) are mounted in an organ bath in a way to allow the measurement of isometric contractions. Contractile activity is elicited by a potassium depolarization in Tyrode's solution. This experimetnal set-up is a well known standard model for the identification of substances blocking the calcium channels opened during the potassium depolarization (Fleckenstein, Calcium Antagonism in Heart and Smooth Muscle, J. Wiley & Sons, 1983).

(b) Isolated Papillary Muscles (Table 2)

Papillary muscles from the left ventricle of the guinea-pig are mounted, like isolated vessels, in an organ bath in a way to allow the measurement of isometric contractions. Electric excitation is achieved by means of field excitation at a frequency of 250/minute (duration of excitation 10 msec., amplitude supramaximal).

(c) Spontaneously Hypertensive Rat (Table 3)

This test model employing hypertension of genetic origin served to test Example Number 1(a) for its antihypertensive efficacy. Table 3 illustrates that a good and, dose-dependent, lasting antihypertensive effect can be observed after oral administration.

(d) Anesthetized Rat

This test model using rats anesthetized with inactin served to test Example Number 1a in a dosage of 100 mg/kg ID (n=3). The heart rate remained unchanged whereas the blood pressure fell by 40% below the starting value (75 minutes PA).

TABLE 1

Concentrations ($IC_{50}$, mol/l) of compounds effecting a semimaximal inhibition of the K+ − depolarization contraction of vessel rings in the organ bath. A. bas. = arteria basilaris, a. cor. = arteria coronaria, a. saph. = arteria saphena of the rabbit; mean diameter 0.5–1.0 mm.

| Example Number | a. basilaris | a. coronaria | a. saphena |
|---|---|---|---|
| 1 | $8 \times 10^{-6}$ | $1 \times 10^{-5}$ | $7 \times 10^{-6}$ |
| 1a | $1.8 \times 10^{-6}$ | $1.5 \times 10^{-6}$ | $1.2 \times 10^{-6}$ |
| 3 | $2 \times 10^{-5}$ | $2 \times 10^{-5}$ | $9 \times 10^{-6}$ |
| 1b | $\sim 4 \times 10^{-7}$ | $\sim 1 \times 10^{-6}$ | |
| 3a | $4 \times 10^{-8}$ | $4.5 \times 10^{-8}$ | |

TABLE 2

Changes in the contraction amplitude of isolated papillary muscles of the guinea-pig (excitation frequency 250/minute, duration of excitation 10 msec., excitation amplitude 10–20 V field excitation). IC = inhibition concentration, ED = effective concentration in mol/l. Indices 50 and 100 correspond to semi-maximal and maximal effect. Δ% = percent change of contraction amplitude versus control.

| Example Number | $IC_{100}$ | Δ% | $IC_{50}$ | Δ% |
|---|---|---|---|---|
| 1 | $10^{-4}$ | −27 | $2 \cdot 10^{-5}$ | −13 |
| | $ED_{100}$ | Δ% | $ED_{50}$ | Δ% |
| 1a | $10^{-6}$ | +52 | $1.5 \cdot 10^{-8}$ | +26 |
| 3 | $10^{-6}$ | +30 | $2.2 \cdot 10^{-8}$ | +15 |

TABLE 3

Effect of Example Number 1a on the systolic blood pressure of spontaneously hypertensive rats (SHR)

| Example Number | Dose mg/kg Oral | Change of systol. blood pressure in percent Time After Application | | | |
|---|---|---|---|---|---|
| | | 30 min. | 120 min. | 240 min. | 24 h |
| 1a | 100 | −40 | −19 | +2 | −4 |
| | 50 | −32 | −8 | +1 | +4 |
| | 25 | −24 | −2 | −1 | +5 |
| | 12.5 | −11 | −4 | +2 | −1 |

We claim:
1. A compound of the formula

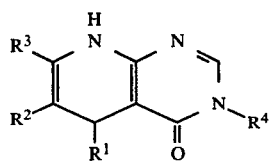

wherein
R[1] is phenyl, pyridyl or thienyl, or phenyl substituted by up to three of the same or different groups selected from a straight or branched alkyl with up to four carbon atoms, halogen, nitro, a straight or branched alkoxy with up to four carbon atoms, difluoromethoxy trifluoromethoxy, dialkylamino, alkylthio and trifluoromethyl, or a methylenedioxy group;
R[2] is a nitrile group, a carboxyl group or an alkoxycarboxyl residue with up to six carbon atoms;
R[3] is a straight-chained or branched alkyl group with up to four carbon atoms or an amino group; and
R[4] represents hydrogen, an alkyl, alkoxyalkyl or substituted or unsubstituted aminoalkyl group; or a pharmaceutically acceptable salt thereof.

2. A compound as claimed in claim 1 wherein
R[1] represents phenyl or phenyl substituted in two or three position, by halogen, nitro, methyl, methoxy, difluoromethoxy, trifluoromethoxy, dimethylamino or diethylamino, methylthio, or trifluoromethyl, or disubstituted, in 2,3 position, by methoxy or methylenedioxy, or in 2,3 or 2,6 position by halogen atoms, which may be the same or different;
R[2] represents a nitrile group, a carboxyl group or an alkoxycarbonyl residue or the formula $$-CO_2R^5 \qquad (II)$$

in which R[5] represents a methyl, ethyl, n-propyl, isopropyl, n-butyl, isobutyl, tert. butyl, or a lower alkoxyalkyl residue;
R[3] represents a methyl or ethyl residue or an amino group;
R[4] represents hydrogen, a methyl, ethyl, n-propyl or isopropyl residue, an alkoxyalkyl group of the formula $$-(CH_2)_n-O-R^6 \qquad (III)$$

in which R[6] represents a lower straight-chained or branched alkyl group and n represents the value two or three, or an aminoalkyl group of the formula

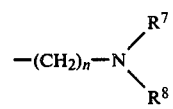

in which R[7] and R[8] may be the same or different, and represent a straight-chained or branched lower alkyl group, or together form a lower alkylene group, and n is two or three.

3. A compound according to claim 1 and being the ethyl ester of 5-(2-fluorophenyl)-3,4,5,8-tetrahydro-7-methyl-4-oxo-pyrido[2,3-d]pyrimidine-6-carboxylic acid.

4. A pharmaceutical composition comprising a vasospasmolytically effective amount of a compound as claimed in claim 1 with a pharmaceutically acceptable carrier or diluent.

5. A method for treating vascular diseases caused by potassium deplorization induced by calcium which comprises administering to a host suffering therefrom a calcium antagonist effective amount of a pharmaceutical composition as claimed in claim 4 in unit dosage form.

* * * * *